United States Patent
Haslwanter et al.

(10) Patent No.: US 6,565,832 B1
(45) Date of Patent: May 20, 2003

(54) SPRAY COMPOSITION WITH REDUCED DRIPPING

(75) Inventors: Joseph A. Haslwanter, Germantown, TN (US); William J. McLaughlin, Germantown, TN (US); David M. Oakley, Germantown, TN (US); Kurt G. Van Scoik, Germantown, TN (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 09/494,574

(22) Filed: Jan. 31, 2000

(51) Int. Cl.[7] .............................. A61K 9/12; A61K 9/08
(52) U.S. Cl. ...................... 424/45; 424/78.04; 424/434; 514/853
(58) Field of Search .................. 424/45, 78.04, 424/78.08, 601, 434; 514/912, 853, 937

(56) References Cited

U.S. PATENT DOCUMENTS

| | | | | |
|---|---|---|---|---|
| 5,854,269 A | * | 12/1998 | Haslwanter et al. | |
| 5,897,858 A | * | 4/1999 | Haslwanter et al. | |
| 5,976,573 A | * | 11/1999 | Kim | |
| 6,368,616 B1 | * | 4/2002 | Doi | 424/434 |

* cited by examiner

Primary Examiner—Michael G. Hartley
Assistant Examiner—M. Haghighatian
(74) Attorney, Agent, or Firm—Robert A. Franks

(57) ABSTRACT

An aqueous-based sprayable composition comprises a therapeutic or palliative agent, water and a mixture of microcrystalline cellulose and alkali metal carboxyalkylcellulose. In one embodiment, the composition is a non-Newtonian nasal spray exhibiting a very rapid viscosity recovery upon removal of shear forces.

Figure 1:
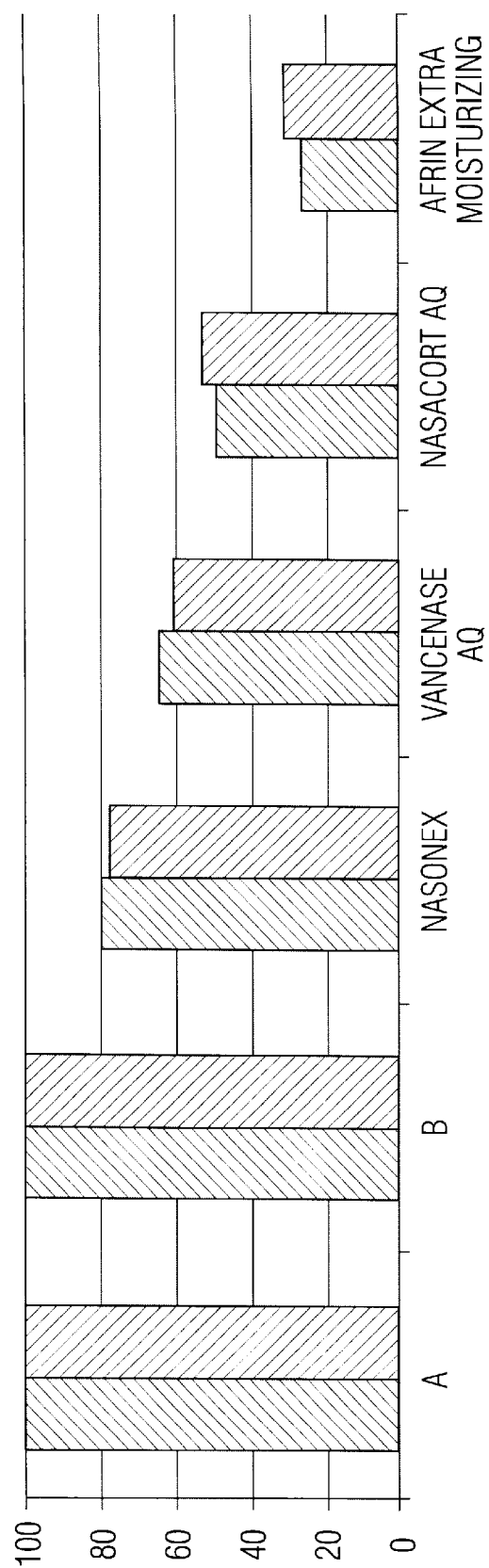

5 Claims, 2 Drawing Sheets

SPRAY COMPOSITION WITH REDUCED DRIPPING

INTRODUCTION TO THE INVENTION

The present invention relates to the field of fluid compositions for application to the body, and more particularly to spray compositions which have a reduced tendency to run or drip.

Nasal sprays have been used for many years by persons suffering from nasal disorders, such as infections or allergic manifestations. Among the pharmaceutical agents commonly delivered intranasally are antihistamines, antiinflammatory drugs, decongestants, antimuscarinics, antibiotics, anesthetics and moisturizers. In addition, it is possible to deliver agents intranasally to achieve systemic effects through absorption across the well-vascularized mucosal membranes; certain vaccines, analgesics and other prophylactic or therapeutic substances can be efficiently administered in this manner.

Various spray compositions are also known for application other than intranasally, such as breath freshener and analgesic sprays for the mouth and pharynx and antiseptic sprays for skin application of medicinal or cosmetic compositions.

A common problem with spray administration is a low efficiency of the active agent, since the structure of body cavities and parts does not typically facilitate retention of the applied formulation. This is particularly the case for aqueous-base nasal spray formulations, which must have sufficient fluidity to be dispensed by a pump device or a squeeze-type spray bottle, but which can simply drain from the nose or pass through the nose and into the pharynx while, or immediately after, being sprayed. Moreover, due to ciliation of the nasal passages and movement of air through the nose, even materials applied in particulate form, such as by a pressurized metered dose inhaler or a powdered drug inhaler, are rapidly cleared from the nose. Several of the possible active agents or other formulation components have a quite unpleasant taste, so it is desirable to minimize the amount of the formulation which is not retained within the nose for at least the minimum time required to obtain the desired effect. Due to swallowing of much of the formulation which enters the oropharyngeal area, a large portion of the active agent introduced into the nose is generally rendered unavailable for its intended use.

Aqueous materials sprayed onto the oral, rectal or vaginal mucosa, or onto the skin, similarly have a tendency to run or drip, and therefore frequently are not retained in a desired location for sufficient time to accomplish the desired function, which may involve absorption of an active agent by the underlying tissues for a local or systemic effect.

International Patent Application WO 94/05330 describes a nasal spray product that forms a gel upon contact with mucous membranes, which product contains a crosslinked acrylic acid-based polymer. The product is alleged to exhibit a reduced tendency for "roll-back," where liquid exits the nose after spray application.

The product Nasacor™ AQ nasal spray is an aqueous suspension of particles of the corticosteroid drug triamcinolone acetonide, and contains about 2 percent by weight of a mixture of microcrystalline cellulose and carboxymethylcellulose sodium, as a suspending agent. Such suspensions are described in U.S. Pat. No. 5,976,573.

The product Vancenase™ AQ nasal spray is an aqueous suspension of the corticosteroid drug beclomethasone dipropionate monohydrate, containing about 1.5 percent by weight of a mixture of microcrystalline cellulose and carboxymethylcellulose sodium, as a suspending agent.

The product Nasonex™ nasal spray is an aqueous suspension of the corticosteroid drug mometasone furoate monohydrate, containing about 2 percent by weight of a mixture of microcrystalline cellulose and carboxymethylcellulose sodium, as a suspending agent.

It would be desirable to provide an aqueous composition that can be made to have a viscosity sufficiently low to permit spraying with a standard pump mechanism or squeeze-type spray bottle, but which then rapidly exhibits a significant viscosity increase to retain the composition at the application site.

SUMMARY OF THE INVENTION

The present invention provides an aqueous-based sprayable composition containing a therapeutic or palliative agent, water and a mixture of microcrystalline cellulose and alkali metal carboxyalkylcellulose. The composition is a non-Newtonian, or thixotropic, fluid, exhibiting a reduced apparent viscosity while being subjected to shear forces, but a high apparent viscosity while at rest; this property permits application by spraying with readily available pump spray devices or squeeze-type spray bottles immediately following the application of a shearing force (such as those created by vigorously shaking the product container), but causes the sprayed material to remain at least temporarily relatively immobile on mucosal membranes or the skin. The preferred embodiments have a very rapid rate of viscosity recovery, following withdrawal of the shearing force.

The invention can be used to prepare many types of spray compositions, such as those for application to mucous membranes or the skin. In a particularly preferred form, the invention is an aqueous nasal spray containing a topically active decongestant.

BRIEF DESCRIPTION OF THE DRAWINGS

FIG. 1 is a graphical representation of the results of the experiment described in Example 4.

FIG. 2 is a graphical representation of the results of the experiment described in Example 5.

DETAILED DESCRIPTION OF THE INVENTION

The essential components of the composition of the present invention are water, a therapeutic or palliative agent and a mixture of microcrystalline cellulose and an alkali metal carboxyalkylcellulose. It is contemplated that the composition will be useful for delivering agents by spraying; it is an advantage of the invention that the composition, after spraying, has a minimal tendency to drip or run from the surface to which it is applied.

Typically, purified water, such as that treated by distillation, deionization or reverse osmosis techniques will be used, it generally being desired to minimize formulation characteristic variations which may occur when the water supply is not very consistent in its chemical makeup. Preferred waters include those having the specifications of the official monograph for "Purified Water" in the current *United States Pharmacopeia*, published by United States Pharmacopeial Convention, Inc., Rockville, Md. U.S.A. In those instances where microbial contamination must be prevented, such as for antiseptic skin sprays, sterile water will be used and any of the customary preservatives will be added.

Numerous classes of pharmaceutical active agents are suitable for inclusion in the thixotropic formulation of the invention. Agents for delivery intranasally include antihistamines, antiinflammatory drugs, decongestants, antimuscarinics, antibiotics, anesthetics and moisturizers. Orally delivered agents include antibiotics, analgesics, anesthetics and moisturizers. Agents which are delivered vaginally or rectally include antiemetics, antibiotics (including antimycotic agents), analgesics and anesthetics. For topical application to the skin, useful active agents include sunscreening agents, local anesthetics and antimicrobials. These lists are not intended to be exhaustive, as many other types of active agents can beneficially be incorporated into the inventive formulations. Frequently, it will be desired to incorporate a mixture of two or more active agents, sometimes including more than one class of such agents, in a composition.

Particularly efficacious in the nasal spray compositions of the present invention are the sympathomimetic amine nasal decongestants. Those currently approved for topical use in the United States include, without limitation, levmetamfetamine (also known as 1-desoxyephedrine), ephedrine, ephedrine hydrochloride, ephedrine sulfate, naphazoline hydrochloride, oxymetazoline hydrochloride, phenylephrine hydrochloride, propylhexedrine and xylometazoline hydrochloride. Levmetamfetamine and propylhexidrine are typically administered by inhalation, being dispersed in air, so are candidates for pressurized aerosol formulation, while the other compounds are usually administered topically in aqueous solutions or jellies, in concentrations differing for the individual drugs, but typically not exceeding about 1 percent by weight.

Specific drugs that may be incorporated when the composition is intended to relieve oropharyngeal discomfort, such as sore throat, cold or canker sores, painful gums and other conditions are topical anesthetics such as phenol, hexylresorcinol, salicyl alcohol, benzyl alcohol, dyclonine, dibucaine, benzocaine, buticaine, cetylpyridinium chloride, diperidon, clove oil, menthol, camphor, eugenol and others. Similarly, drugs that may be incorporated for application to the skin for relieving discomfort include lidocaine, benzocaine, tetracaine, dibucaine, pramoxine, diphenhydramine, benzyl alcohol, hydrocortisone, betamethasone, mometasone and others.

Mixtures of microcrystalline cellulose and an alkali metal carboxyalkylcellulose are commercially available, the mixture presently preferred for use in this invention being sold by FMC Corporation, Philadelphia, Pa. U.S.A. as Avicel™ RC-591. This material contains approximately 89 weight percent microcrystalline cellulose and approximately 11 weight percent sodium carboxymethylcellulose, and is known for use as a suspending agent in preparing various pharmaceutical suspensions and emulsions. However, there previously has been no reported application for this material in compositions which otherwise have no suspended particulates, i.e., which compositions are solutions. The compositions of the present invention contain at least about 2.5 weight percent of the cellulose/carboxyalkylcellulose compound mixture, generally not exceeding about 10 weight percent to avoid producing high viscosities which impede spraying with the usual devices. Preferably, about 2.5 to about 5 percent of the mixture will be included. More preferably, the amount will be about 2.5 to about 3.5 weight percent.

A closely related mixture is available from the same source as Avicel™ RC-581, having the same bulk chemical composition as the RC-591, and this material is also useful in the invention. Microcrystalline cellulose and alkali metal carboxyalkylcellulose are commercially available separately, and can be mixed in desired proportions for use in the invention, with the amount of microcrystalline cellulose preferably being between about 85 and about 95 weight percent of the mixture for both separately mixed and co-processed mixtures. However, performance of the inventive composition appears to generally be better when the co-processed mixtures are used.

When the compositions of the invention are intended for application to sensitive mucosal membranes, it will usually be desirable to adjust the pH to a relatively neutral value, using an acid or base, unless the natural pH already is suitable. In general, pH values about 4 to about 8 are preferred for tissue compatibility; the exact values chosen should also promote chemical and physical stability of the composition. In some instances, buffering agents will be included to assist with maintenance of selected pH values; typical buffers are well known in the art and include, without limitation thereto, phosphate, citrate and borate salt systems.

Depending on the intended application, it may be desirable to incorporate up to about 10 percent by weight, more typically about 0.5 to about 5 weight percent, of an additional rheology-modifying agent, such as a polymer or other material. Useful materials include, without limitation thereto, sodium carboxymethyl cellulose, algin, carageenans, carbomers, galactomannans, hydroxypropyl methylcellulose, hydroxypropyl cellulose, polyethylene glycols, polyvinyl alcohol, polyvinylpyrrolidone, sodium carboxymethyl chitin, sodium carboxymethyl dextran, sodium carboxymethyl starch and xanthan gum. Combinations of any two or more of the foregoing are also useful.

The compositions may further contain any of a number of optional components, such as humectants, preservatives and aromatic substances. Humectants, which are hygroscopic materials such as glycerin, a polyethylene or other glycol, a polysaccharide and the like act to inhibit water loss from the composition and may add moisturizing qualities. Useful aromatic substances include camphor, menthol, eucalyptol and the like, and fragrances. Preservatives are typically incorporated to establish and maintain a freedom from pathogenic organisms; representative components include benzyl alcohol, methylparaben, propylparaben, butylparaben, chlorobutanol, phenethyl alcohol (which also is a fragrance additive), phenyl mercuric acetate and benzalkonium chloride.

The more simple techniques commonly used to determine rheological properties of fluid compositions, including the Brookfield rotating kinematic viscometer which measures torque transmitted through a sample using a rotating spindle, do not yield the most meaningful information for non-Newtonian fluids such as those of this invention. Since the viscosity of the thixotropic composition varies inversely according to the magnitude of shear force being applied, and the viscosity increases over time following withdrawal of the shear force, it is more useful to measure and compare complex viscosity. A mathematical derivation of complex viscosity can be found in H. A. Barnes et al., *An Introduction to Rheology*, Elsevier, N.Y. 1989, particularly at pages 46–48. Complex viscosity from a oscillatory applied shear is defined by these authors at page 48 as being: "the ratio of the shear stress . . . to the rate of shear. . . . " Units for expressing complex viscosity (typically represented by the symbol $\eta^*$) are in Pascal seconds (Pa.s.), equivalent to newton seconds/meter$^2$ in the International System of Units.

The composition of the invention has a shear viscosity sufficiently low to permit spraying with the customary pumps or squeeze bottles commonly used to deliver products such as nasal sprays. It should be noted that this shear viscosity frequently will not be the minimum viscosity attainable under shear conditions, since it is expected that sprayability will be achieved from a more or less vigorous shaking by the user, immediately prior to dispensing. Different populations have differing physical abilities to impart shear to the product, so candidate compositions will necessarily be tested with various spray devices, to determine which combination will be satisfactory for the intended purpose. Further, different amounts of the mixture of microcrystalline cellulose and alkali metal carboxyalkylcellulose (and varying ratios of the components of this mixture) may be used, as well as the incorporation of other rheology modifiers, to obtain a desired viscosity behavior.

The invention will be further described by means of the following examples, which are not intended to limit the scope of the invention, as defined by the appended claims, in any manner. In the examples, as elsewhere in this specification, chemical substances are generally identified, whenever possible, by their adopted names, such as are given in J. A. Wenninger et al., Eds., *International Cosmetic Ingredient Dictionary and Handbook*, Seventh Ed., The Cosmetic, Toiletry and Fragrance Association, Washington, D.C., U.S.A., 1997. Percentages are expressed on a weight basis, unless the context clearly indicates otherwise. The mention of any specific drug substance in this specification or in the claims is intended to encompass not only the base drug, but also pharmaceutically acceptable salts, esters, hydrates and other forms of the drug. Where a particular salt or other form of a drug is mentioned, it is contemplated that other salts or forms can be substituted.

EXAMPLE 1

A nasal spray composition is prepared using the following ingredients (amounts expressed in grams), together with sufficient purified water to make a total of 1000 grams.

| Ingredient | |
| --- | --- |
| Oxymetazoline hydrochloride | 0.4878 |
| Avicel RC-591 | 29.2683 |
| Polyvinylpyrrolidone* | 29.2683 |
| PEG-32** | 48.7805 |
| Sodium phosphate, dibasic | 0.9512 |
| Sodium phosphate, monobasic | 5.3902 |
| Disodium EDTA | 0.2927 |
| Benzalkonium chloride, 17% aq. solution | 1.4351 |
| Benzyl alcohol | 2.439 |
| Lemon flavor | 1.4634 |

*Plasdone ™ K29–32 sold by International Specialty Products, Wayne, New Jersey U.S.A.
**CARBOWAX ™ PEG 1450 sold by Union Carbide Corporation, Houston, Texas U.S.A.

The composition is prepared as follows:
(a) the Avicel RC-591 is dispersed in about 725 grams of the water, by means of slow addition to the vigorously stirred water and circulation of the dispersion through a high-shear disperser for at least 60 minutes after all of the Avicel material has been added, to form a uniform dispersion;
(b) in a separate vessel, the polyvinylpyrrolidone is dissolved in about 85 grams of the water and stirred until a clear solution is obtained;
(c) the polyethylene glycol is added to the solution of (b) and stirred until a clear solution is obtained;
(d) The solution of (c) is added to the dispersion of (a);
(e) in another vessel, the disodium EDTA is dissolved in about 12 grams of water and, after a solution is obtained, the sodium phosphates are added and dissolved;
(f) the solution of (e) is added to the dispersion of (d);
(g) to about 5 grams of water in a separate vessel is added the oxymetazoline hydrochloride and the mixture is stirred to obtain a solution;
(h) the solution of (g), the benzyl alcohol, the benzalkonium chloride and the lemon flavor are sequentially added to the dispersion of (f), with a period of stirring being completed between additions;
(i) additional water is added to achieve a batch of 1000 grams and the product is thoroughly stirred; and
(j) the entire batch is passed through the high-shear disperser to ensure that any coagulated particles are re-dispersed.

EXAMPLE 2

Nasal spray compositions are prepared in accordance with the invention, using the general procedure of the preceding example and the following ingredients (where amounts are weight percentages):

| Ingredient | A | B | C |
| --- | --- | --- | --- |
| Water | 89.7229 | 90.2279 | 89.7229 |
| Oxymetazoline hydrochloride | 0.05 | 0.05 | 0.05 |
| Avicel ™-591 | 3 | 3 | 3 |
| Polyvinylpyrrolidone* | 3 | 3 | 3 |
| PEG-32** | 5 | 5 | 5 |
| Sodium phosphate, dibasic | 0.0975 | 0.0975 | 0.0975 |
| Sodium phosphate, monobasic | 0.5525 | 0.5525 | 0.5525 |
| Disodium EDTA | 0.03 | 0.03 | 0.03 |
| Benzalkonium chloride, 17% aq. solution | 0.1471 | 0.1471 | 0.1471 |
| Benzyl alcohol | 0.25 | 0.35 | 0.3 |
| Lemon flavor | 0.15 | — | — |
| Glycerin | 0.5 | — | — |
| Propylene glycol | — | — | 0.5 |
| Camphor | — | 0.009 | 0.02 |
| Menthol | — | 0.027 | 0.06 |
| Eucalyptol | — | 0.009 | 0.02 |

*Plasdone ™ K29-32 sold by International Specialty Products, Wayne, New Jersey U.S.A.
**CARBOWAX ™ PEG 1450 sold by Union Carbide Corporation, Houston, Texas U.S.A.

EXAMPLE 3

Nasal spray compositions are prepared in accordance with the invention, using the general procedure of preceding Example 1 and the following ingredients (where amounts are weight percentages):

| Ingredient | D | E | F | G |
| --- | --- | --- | --- | --- |
| Water | 95.8272 | 90.9492 | 92.9004 | 88.5102 |
| Oxymetazoline hydrochloride | 0.0488 | 0.0488 | 0.0488 | 0.0488 |
| Avicel ™-591 | 2.9268 | 2.9268 | 2.9268 | 2.439 |
| Polyvinylpyrrolidone* | — | — | 2.9268 | 2.9268 |
| PEG-32** | — | 4.878 | — | 4.878 |
| Sodium phosphate, dibasic | 0.0951 | 0.0951 | 0.0951 | 0.0951 |
| Sodium phosphate, monobasic | 0.539 | 0.539 | 0.539 | 0.539 |
| Disodium EDTA | 0.0293 | 0.0293 | 0.0293 | 0.0293 |

-continued

| Ingredient | D | E | F | G |
|---|---|---|---|---|
| Benzalkonium chloride, 17% aq. solution | 0.1435 | 0.1435 | 0.1435 | 0.1435 |
| Benzyl alcohol | 0.2439 | 0.2439 | 0.2439 | 0.2439 |
| Lemon flavor | 0.1463 | 0.1463 | 0.1463 | 0.1463 |

*Plasdone ™ K29–32 sold by International Specialty Products, Wayne, New Jersey U.S.A.
**CARBOWAX ™ PEG 1450 sold by Union Carbide Corporation, Houston, Texas U.S.A.

EXAMPLE 4

Commercially available nasal spray compositions are tested against the composition of preceding Example 1, to identify differences in their dripping potentials. In the test, borosilicate glass test tubes are weighed, then clamped in an inverted vertical position. The nasal spray bottle is weighed, placed under the mouth of the test tube, sprayed twice and then immediately removed. After 60 seconds, the test tube is turned vertically to position the mouth at the top and is weighed to quantify the amount of nasal spray that did not drip out. The nasal spray bottle is weighed to determine the amount delivered by the two spray actuations, and the percentage of the delivered dose remaining in the test tube is calculated.

Results are as shown in the following table and in the graph of FIG. 1, where bars "A" and "B" represent the percentage of sprayed material remaining in the tube for two different preparations of the composition of Example 1. The remaining legends of the graph identify the tested commercially available compositions. Each composition is tested in duplicate, and the results of each of the two trials for a product are shaded differently in the graph.

The Afrin™ Extra Moisturizing Nasal Spray product contains 0.05 weight percent oxymetazoline, in addition to benzalkonium chloride, disodium EDTA, povidone, sodium phosphate dibasic, sodium phosphate monobasic, glycerin, polyethylene glycol 1450, propylene glycol and water. This product, sold in a "squeeze-type" spray bottle, is transferred to a pump spray bottle identical to those used for the Example 1 compositions, for this test. All other commercial products are tested in their original pump spray bottles.

| Product | mg Sprayed | mg Remaining | % Remaining |
|---|---|---|---|
| Example 1, "A" | 214.1, 214.4 | 212.6, 213.5 | 99.3, 99.6 |
| Example 1, "B" | 217.5, 219.8 | 216.0, 219.4 | 99.3, 99.8 |
| Nasonex ™ | 204.3, 202.4 | 162.9, 158.9 | 79.7, 78.5 |
| Vancenase AQ ™ | 202.9, 214.8 | 132.6, 132.5 | 65.4, 61.7 |
| Nasacort AQ ™ | 196.9, 195.5 | 97.4, 103.8 | 49.5, 53.1 |
| Afrin ™ Extra Moisturizing | 207.8, 208.9 | 55.6, 63.9 | 26.8, 30.6 |

It is clear that the products of Example 1 have a significantly lower dripping potential than any other tested product. Moreover, since no dripping was visible for the Example 1 compositions, it is possible that the small differences between amounts of material sprayed and material remaining are due to evaporation of contained water during the course of the experiment.

EXAMPLE 5

An experiment is performed to measure the rate at which viscosity is recovered, upon termination of an applied shearing force. The experiment utilizes a dynamic stress rheometer Model SR-5000 available from Rheometric Scientific, Inc., Piscataway, N.J. U.S.A., the sample being contained in a cone and plate fixture. The instrument is set to apply a shearing stress to the sample that begins at zero and ramps upward to 1000 dynes/cm$^2$ during a 5 second period. The stress ramps down to 5 dynes/cm$^2$ during the next 2 seconds, then from 5 to 4 dynes/cm$^2$ during the following 50 seconds. A graphical comparison of the complex viscosities of the composition of Example 1 (upper curve) and of the commercial NASONEX™ nasal spray, containing 2 weight percent of a mixture of microcrystalline cellulose and carboxymethylcellulose sodium, (lower curve) is shown as FIG. 2, where the y-axis is complex viscosity and the x-axis is time in seconds during the period where applied stress is ramping downward from 5 to 4 dynes/cm$^2$.

Figure 2:
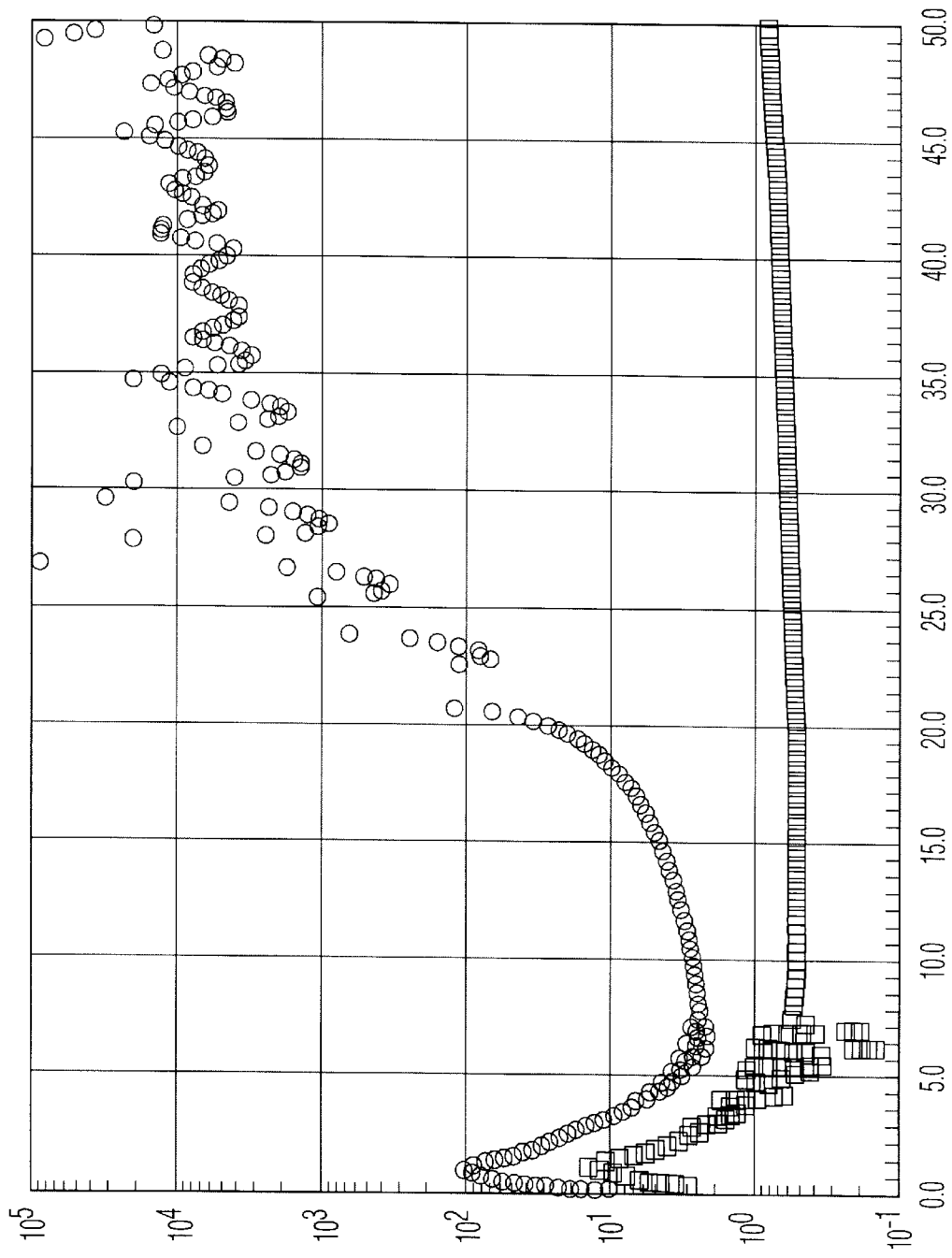

Referring to FIG. 2, it can be seen that at 20 seconds the Example 1 composition has recovered its complex viscosity in an amount approximately an order of magnitude greater than that recovered by the NASONEX composition. Thus, the higher concentration of a mixture of microcrystalline cellulose and carboxymethylcellulose sodium gives the Example 1 composition a greatly reduced tendency to flow after spraying.

These graphical results may constitute an explanation for the higher amount of Nasonex product that drips from the tube in the experiment of the immediately preceding example.

What is claimed is:

1. A nasal spray composition comprising water, oxymetazoline hydrochloride, about 2.5 to about 3.5 weight percent of a mixture of microcrystalline cellulose and an alkali metal carboxyalkylcellulose, and about 0.5 to about 5 weight percent of polyvinylpyrrolidone, wherein complex viscosity of the composition increases to at least about 10 times a minimum complex viscosity of the composition as measured under high shear conditions, within about 20 seconds after the high shear conditions terminate.

2. The nasal spray composition of claim 1, wherein the alkali metal carboxyalkylcellulose is sodium carboxymethylcellulose.

3. The nasal spray composition of claim 2, wherein microcrystalline cellulose comprises between about 85 and about 95 percent by weight of the mixture with sodium carboxymethylcellulose.

4. A nasal spray composition comprising: water; a nasal decongestant comprising oxymetazoline hydrochloride; about 2.5 to about 3.5 percent by weight of a mixture of microcrystalline cellulose and an alkali metal carboxyalkylcellulose; and about 0.5 to about 5 percent by weight of a rheology-modifying polymer; wherein complex viscosity of the composition increases to at least about 10 times a minimum complex viscosity of the composition as measured under high shear conditions, within about 20 seconds after the high shear conditions terminate.

5. A nasal spray composition comprising: water, a nasal decongestant comprising oxymetazoline hydrochloride; about 2.5 to about 3.5 percent by weight of a mixture of microcrystalline cellulose and an alkali metal carboxyalkylcellulose; and about 0.5 to about 5 percent by weight of a rheology-modifying polymer comprising polyvinylpyrrolidone; wherein complex viscosity of the composition increases to at least about 10 times a minimum complex viscosity of the composition as measured under high shear conditions, within about 20 seconds after the high shear conditions terminate.

* * * * *